United States Patent
Li et al.

(10) Patent No.: US 10,321,993 B2
(45) Date of Patent: Jun. 18, 2019

(54) SELF-EXPANDING HEART VALVES FOR CORONARY PERFUSION AND SEALING

(71) Applicant: St. Jude Medical, Cardiology Division, Inc., St. Paul, MN (US)

(72) Inventors: Xue Mei Li, Shoreview, MN (US); Yousef F. Alkhatib, Edina, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 15/312,360

(22) PCT Filed: May 20, 2015

(86) PCT No.: PCT/US2015/031678
§ 371 (c)(1),
(2) Date: Nov. 18, 2016

(87) PCT Pub. No.: WO2015/179468
PCT Pub. Date: Nov. 26, 2015

(65) Prior Publication Data
US 2017/0079786 A1    Mar. 23, 2017

Related U.S. Application Data

(60) Provisional application No. 62/001,228, filed on May 21, 2014.

(51) Int. Cl.
*A61F 2/24*      (2006.01)

(52) U.S. Cl.
CPC ...... *A61F 2/2418* (2013.01); *A61F 2230/001* (2013.01); *A61F 2230/0013* (2013.01);
(Continued)

(58) Field of Classification Search
CPC ........ A61F 2/24; A61F 2/2409; A61F 2/2418; A61F 2/2469; A61F 2/2493;
(Continued)

(56) References Cited

U.S. PATENT DOCUMENTS

| | | | |
|---|---|---|---|
| 7,442,204 B2* | 10/2008 | Schwammenthal | .. A61F 2/2418 623/1.24 |
| 2003/0023303 A1* | 1/2003 | Palmaz | ................. A61F 2/2418 623/2.18 |

(Continued)

FOREIGN PATENT DOCUMENTS

| WO | 10008549 A1 | 1/2010 |
|---|---|---|
| WO | 10098857 A1 | 9/2010 |

OTHER PUBLICATIONS

Internation Search Report dated Nov. 3, 2015 for Application No. PCT/US2015/031678.

*Primary Examiner* — Paul B Prebilic
(74) *Attorney, Agent, or Firm* — Lerner, David, Littenberg, Krumholz & Mentlik, LLP

(57) ABSTRACT

A prosthetic heart valve includes a collapsible and expandable stent including a plurality of struts forming cells, the stent having a proximal end, a distal end, an annulus section adjacent the proximal end, an aortic section adjacent the distal end, and a transition section disposed between the annulus section and the aortic section, the aortic section having a larger diameter than the annulus section. The heart valve further includes a valve assembly disposed entirely in the annulus section of the stent for controlling the flow of blood through the stent, the valve assembly including a plurality of leaflets, and a cuff, the cuff being disposed on a surface of the stent and extending fully over at least two rows of cells of the stent.

16 Claims, 7 Drawing Sheets

(52) U.S. Cl.
CPC ............... *A61F 2250/0037* (2013.01); *A61F 2250/0039* (2013.01); *A61F 2250/0069* (2013.01)

(58) Field of Classification Search
CPC ...... A61F 2230/0093; A61F 2230/0095; A61F 2250/001; A61F 2250/0039
USPC .............................................. 623/1.24–1.26
See application file for complete search history.

(56) References Cited

U.S. PATENT DOCUMENTS

| | | | |
|---|---|---|---|
| 2004/0039436 A1* | 2/2004 | Spenser ................ | A61F 2/2412 623/1.13 |
| 2006/0259136 A1* | 11/2006 | Nguyen ................ | A61F 2/2412 623/2.18 |
| 2008/0071369 A1* | 3/2008 | Tuval .................... | A61F 2/2418 623/2.38 |
| 2010/0168839 A1* | 7/2010 | Braido .................. | A61F 2/2418 623/1.26 |
| 2010/0204781 A1* | 8/2010 | Alkhatib ............... | A61F 2/2418 623/1.26 |
| 2012/0083875 A1* | 4/2012 | Johnson ................ | A61F 2/2418 623/2.11 |
| 2012/0089223 A1* | 4/2012 | Nguyen ................ | A61F 2/2418 623/2.14 |
| 2015/0073545 A1* | 3/2015 | Braido .................. | A61F 2/2412 623/2.18 |
| 2017/0086971 A1* | 3/2017 | Braido .................. | A61F 2/2418 |
| 2018/0104077 A1* | 4/2018 | Cartledge ............. | A61F 2/2418 |

\* cited by examiner

SELF-EXPANDING HEART VALVES FOR CORONARY PERFUSION AND SEALING

CROSS-REFERENCE TO RELATED APPLICATIONS

The present application is a national phase entry under 35 U.S.C. § 371 of International Application No. PCT/US2015/031678 filed May 20, 2015, published in English, and claims the benefit of the filing date of U.S. Provisional Patent Application No. 62/001,228, filed May 21, 2014, the disclosures of which are hereby incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning collapsible prosthetic heart valves and sealing same in the patient's anatomy to minimize or prevent paravalvular leakage and increase coronary perfusion.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's native heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve, includes a collapsible and expandable stent including a plurality of struts forming cells, the stent having a proximal end, a distal end, an annulus section adjacent the proximal end, an aortic section adjacent the distal end, and a transition section disposed between the annulus section and the aortic section, the aortic section having a larger diameter than the annulus section. A valve assembly may be disposed entirely in the annulus section of the stent for controlling the flow of blood through the stent, the valve assembly including a plurality of leaflets, and a cuff, the cuff being disposed on a surface of the stent and extending fully over at least two rows of cells of the stent.

In some embodiments, a prosthetic heart valve may include a collapsible and expandable stent including a plurality of struts forming cells, the stent having a proximal end, a distal end, an annulus section adjacent the proximal end, an aortic section adjacent the distal end, a transition section disposed between the annulus section and the aortic section, a plurality of commissure features and a plurality of axial struts oriented parallel to a longitudinal axis of the stent. A valve assembly may be disposed entirely in the annulus section of the stent for controlling the flow of blood through the stent, the valve assembly including a plurality of leaflets and a cuff, the cuff being disposed on a surface of the stent and extending fully over at least two rows of cells of the stent.

BRIEF DESCRIPTION OF THE DRAWINGS

Various embodiments of the present disclosure are described herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION

The clinical success of a prosthetic heart valve is dependent on multiple factors including accurate deployment and effective sealing within the patient's anatomy. Inaccurate placement and/or anchoring may result in the leakage of blood between the implanted heart valve and the native valve annulus, commonly referred to as paravalvular or perivalvular leakage. In aortic valves, this leakage enables blood flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage.

Moreover, anatomical variations between patients may require removal of a fully deployed heart valve from the patient if it appears that the valve is not functioning properly. Removing a fully deployed heart valve increases the length of the procedure and increases the risk of infection and/or damage to heart tissue. Thus, methods and devices are desirable that would reduce the need to remove a deployed valve. Methods and devices are also desirable that would reduce the likelihood of paravalvular leakage around the implanted heart valve.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. Also as used herein, the terms "generally," "substantially," and "about" are intended to mean that slight deviations from absolute are included within the scope of the term so modified.

Figure 1:
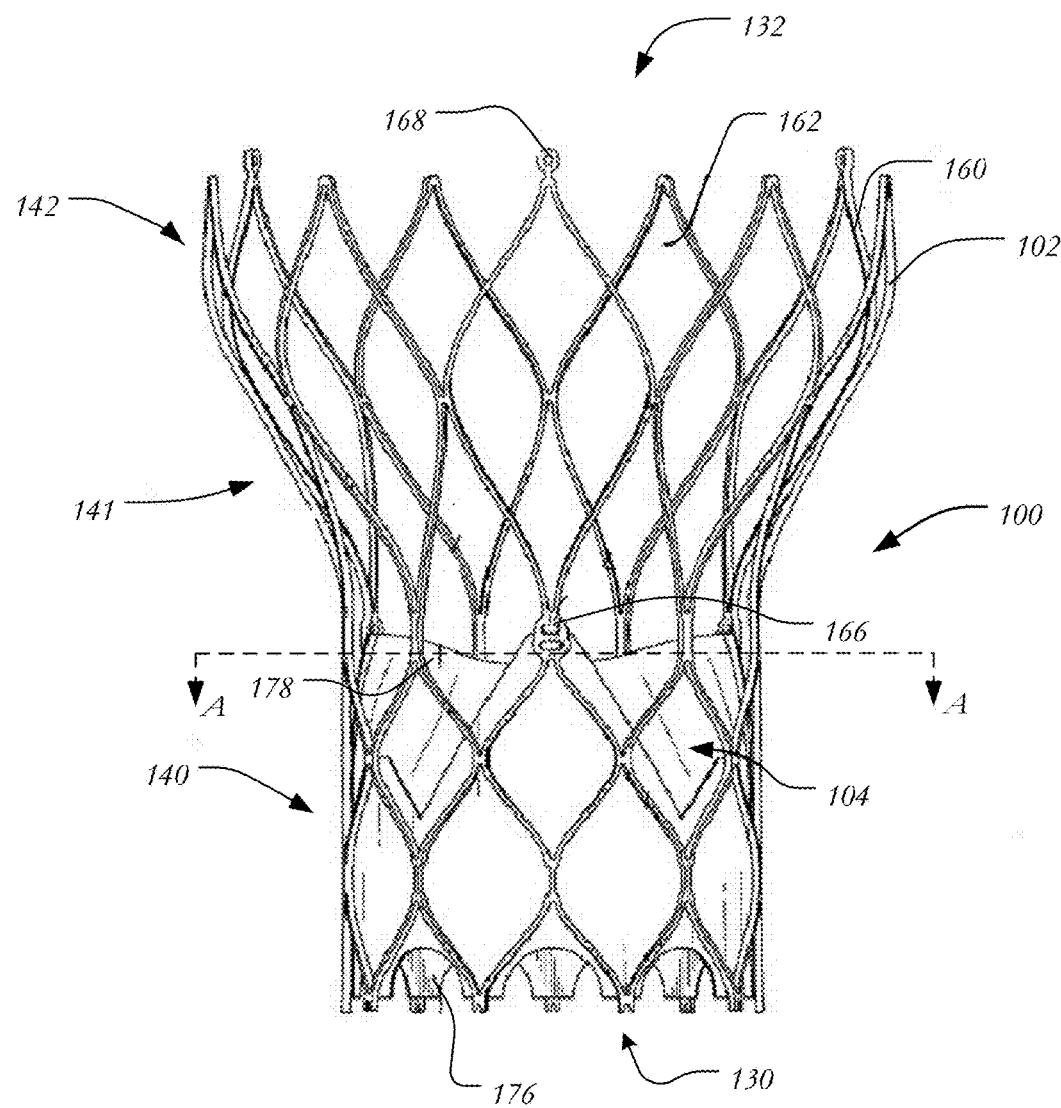
FIG. 1 is a side elevational view of a collapsible prosthetic heart valve.

FIG. 1 shows a collapsible stent-supported prosthetic heart valve 100 including a stent 102 and a valve assembly 104 as known in the art. Prosthetic heart valve 100 is designed to replace a native tricuspid valve of a patient, such as a native aortic valve. It should be noted that, while the inventions herein are described predominately in connection with their use with a prosthetic aortic valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 will be described in more detail with reference to FIG. 1. Prosthetic heart valve 100 includes an expandable stent 102 which may be formed from, for example, a shape memory material, such as the nickel-titanium alloy known as "Nitinol" or other suitable metals, and in particular, from those materials that are capable of self-expansion. Stent 102 extends from a proximal or annulus end 130 to a distal or aortic end 132, and includes an annulus section 140 adjacent proximal end 130, an aortic section 142 adjacent distal end 132, and a transition section 141 between annulus section 140 and aortic section 142. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around stent 102. For example, as shown in FIG. 1, annulus section 140 may have two annular rows of complete cells 162, and aortic section 142 and transition section 141 may each have one or more annular rows of partial cells 162. Cells 162 in aortic section. 142 may be larger than the cells in annulus section 140. The larger cells in aortic section 142 better enable prosthetic valve 100 to be positioned in the native valve architecture without the stent structure interfering with blood flow to the coronary arteries.

Stent 102 may also include a plurality of commissure features 166 for attaching the commissure between two adjacent leaflets to stent 102. As can be seen in FIG. 1, commissure features 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to stent 102.

Stent 102 may include one or more retaining elements 168 at distal end 132 thereof, retaining elements 168 being sized and shaped to cooperate with female retaining structures (net shown) provided on the deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Valve assembly 104 is secured to stent 102, preferably within annulus section 140 of stent 102. Valve assembly 104 includes cuff 176 and a plurality of leaflets 178 which collectively function as a one-way valve by coapting with one another. As a prosthetic aortic valve, valve 100 has three leaflets 178, as well as three commissure features 166. However, it will be appreciated that other prosthetic heart valves having a greater or lesser number of leaflets 178 and commissure features 166 are possible.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed from any suitable biological material, such as porcine or bovine pericardial tissue, or from a polymer such as, for example, polytetrafluoroethylene, nolyurethane, ultra-high molecular weight polyethylene, polyethylene terephthalate, polyester or suitable combinations thereof.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into a patient using a transfemoral, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Figure 2A:
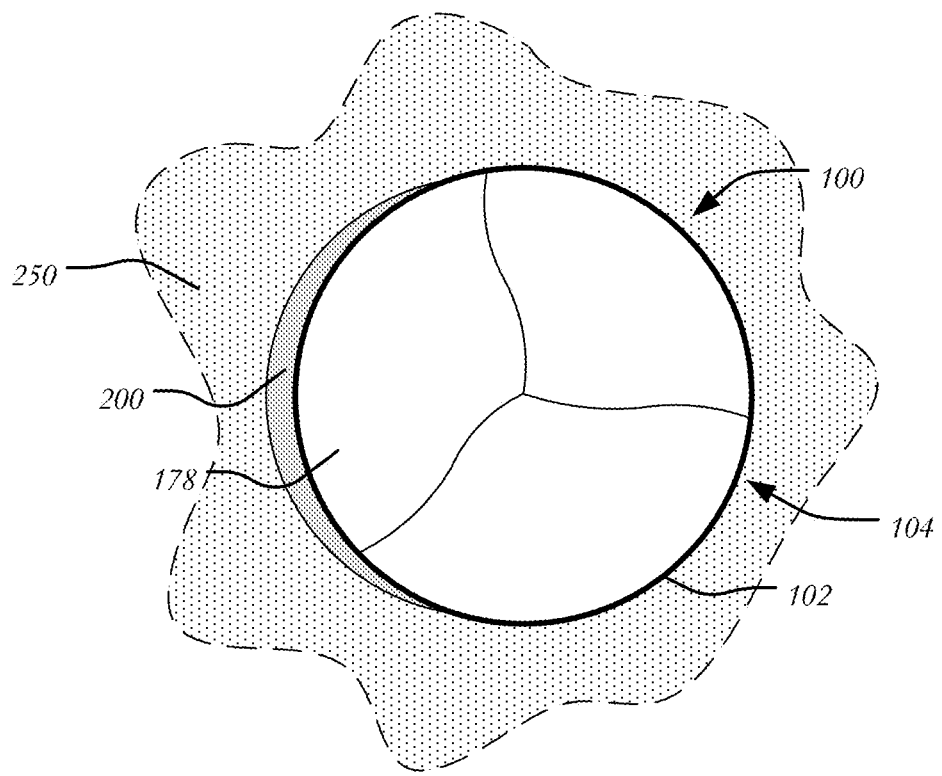
FIG. 2A is a highly schematic cross-sectional view taken along line A-A of FIG. 1 and showing the prosthetic heart valve disposed within a native valve annulus.
Figure 2B:
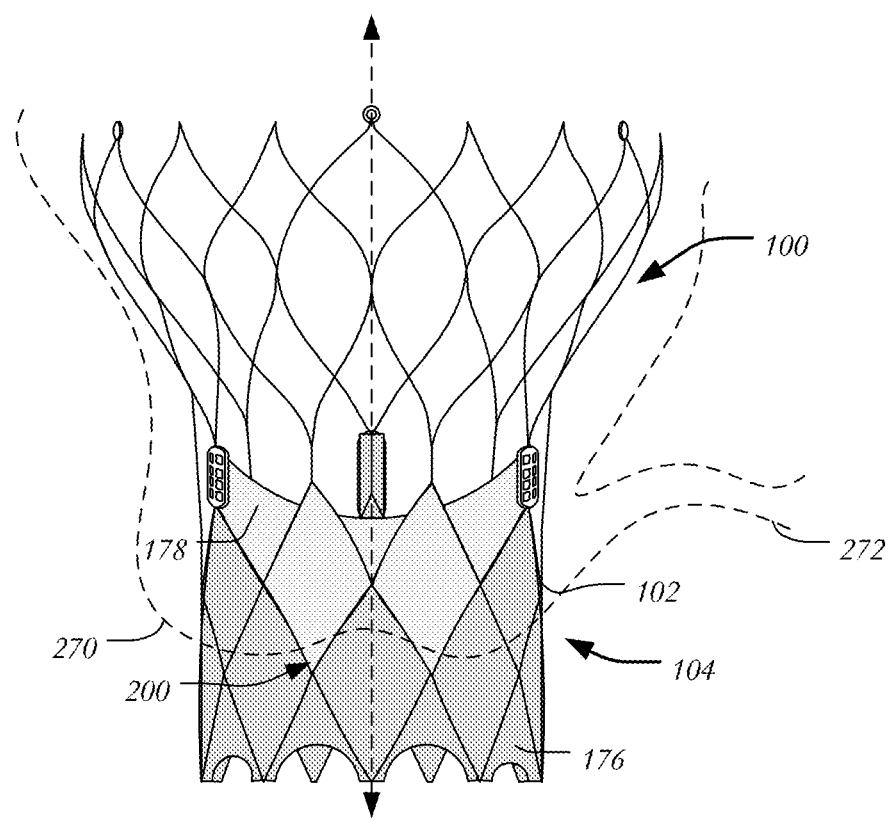
FIG. 2B is a side elevation view of a collapsible prosthetic heart valve after implantation.

FIG. 2A is a highly schematic cross-sectional illustration of prosthetic heart valve 100 disposed within native valve annulus 250. As seen in the figure, in some cases, stent 102 may be implanted in a slightly tilted position or disposed slightly away from the desired site within native valve annulus 250. Due to such imperfect placement, at certain locations around the perimeter of heart valve 100, gaps 200 may form between the heart valve and native valve annulus 250. Blood flowing through these gaps and around leaflets 178 of valve assembly 104 can cause regurgitation and other inefficiencies which reduce cardiac performance. Such improper fitment may also result from suboptimal native valve annulus geometry due, for example, to calcification of native valve annulus 250 or to unresected native leaflets. As shown in FIG. 2B, gaps 200 may also be formed between cuff 176 and aortic root 270. Coronary artery 272 is also shown schematically in order to appreciate the general location of gaps 200 with respect to nearby anatomy.

Figure 3A:
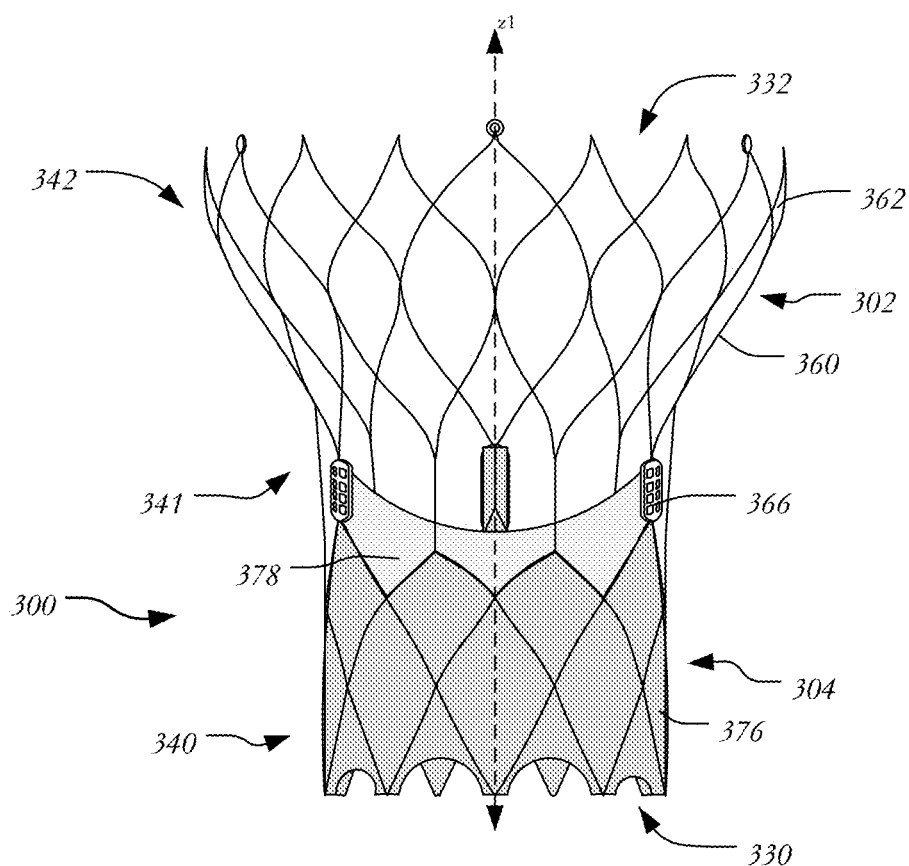
FIG. 3A is a side elevational view of a collapsible prosthetic heart valve having axial struts.

FIG. 3A illustrates one example of a collapsible stent-supported prosthetic heart valve 300 capable of reducing paravalvular leakage and maximizing coronary perfusion. Heart valve 300 includes stent 302 and valve assembly 304 disposed within stent 302. Scent 302 generally extends between proximal end 330 and distal end 332 and includes annulus section. 340 adjacent proximal end 330, aortic section 342 adjacent distal end 332, and transition section 341 between annulus action 340 and aortic section 342. Stent 302 may include a plurality of struts 360 forming a plurality of cells 362, struts 360 being formed of any of the materials described above with reference to FIG. 1. Additionally, stent 302 may include commissure features 366 for attaching leaflets and/or a cuff as will be described below.

Valve assembly 304 may be disposed almost entirely within annulus section 340 as shown and includes a circumferential cuff 376 and a plurality of leaflets 378 formed of any of the materials described above for the cuff and leaflets of FIG. 1. Each leaflet 378 may be attached to cuff 376 and/or to selected struts 360 of stent 302, as well as to commissure features 366, while leaving a free edge for coapting with free edges of other leaflets 378 to form a one-way valve.

In order to improve paravalvular sealing upon suboptimal valve placement, cuff 376 may be extended upward toward distal end 332. However, simply enlarging the cuff may lead to a decrease in coronary perfusion by blocking the coronary arteries. Thus, a balance between paravalvular sealing and coronary perfusion is to be contemplated when determining the size and/or shape of the cuff. Heart valve 300 addresses these concerns through a unique stent and cuff configuration, which will be described in greater detail with reference to FIG. 3B.

Figure 3B:
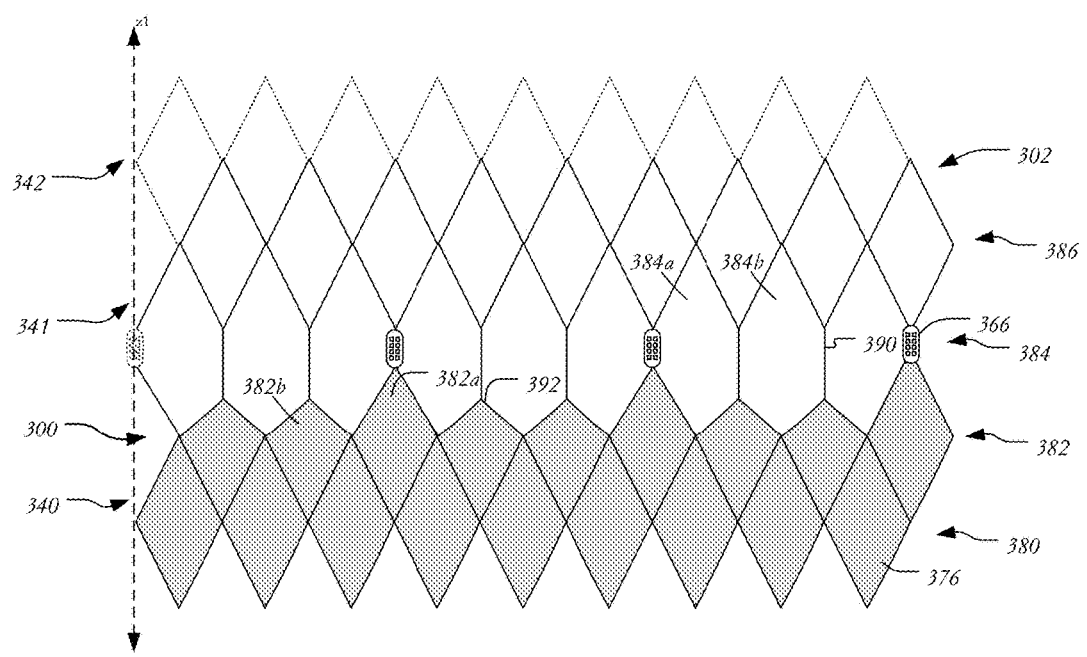
FIG. 3B is a schematic projection of a portion of the heart valve of FIG. 3A.

In FIG. 3B, a schematic projection of a portion of heart valve 300 shows annulus section 340, transition section 341 and a portion of aortic section 342 in dashed lines) of stent 302, commissure features 366 and cuff 376. For the sake of clarity, leaflets and other rows of aortic section 342 are not shown. In this example, stent 302 includes a plurality of rows of cells including a first annular row 380, a second annular row 382, a transition row 384 and an aortic row 386. It will be understood, however, that the number of rows of cells in each section may be increased, decreased as desired, and that entire rows and/or sections may be entirely eliminated. Second annular row 382 includes two types of cells, standard cells 382a and undersized cells 382b. Standard cells 382a may be diamond-shaped and disposed below each of commissure features 366 in second annular row 382. Undersized cells 382b, on the other hand, may each have an area that is smaller than that of standard cells 382a and may form the remaining cells in second annular row 382. In this illustrative example, stent 302 includes three commissure features 366 and hence three standard cells 382a. Stent 302 further includes two undersized cells 382b disposed between adjacent standard cells 382a. Similarly, transition row 384 includes two types of cells, asymmetric cells 384a and hexagonal cells 384b.

The above-configuration is made possible by providing axial struts 390 in transition row 384. In contrast to the diagonally extending struts of stent 302, each axial strut 390 is oriented parallel to central axis z1 of prosthetic heart valve 300 as shown in FIG. 3A. Specifically, axial struts 390 are provided between commissure features 366 and form a group of three cells between adjacent commissure features 366, the group including a single hexagonal cell 384b and a pair of mirror-image asymmetric cells 384a on either side of hexagonal cell 384b. Each axial strut 390 has a length that is greater than that of an adjacent commissure feature 366. Moreover, because each axial strut 390 extends toward second annular row 382, shortened struts 392 form the upper struts of undersized cells 382b. Standard cells 382a remain unchanged in a diamond configuration as they are not connected to axial struts 390.

Cuff 376 may extend over all of the cells in first annular row 380 and second annular rows 382, including standard cells 382a and undersized cells 382b. Sutures may attach cuff 376 to stent. 302 along the bottom edges of row 380, the top edges of undersized cells 382b (i.e., along shortened struts 392) and the top edges of standard cells 382a. Optionally, cuff 376 may also be attached to commissure features 366 of stent 302. The addition of cuff 376 over undersized cells 382b aids in reducing paravalvular leakage due to less-than-perfect placement. Additionally, transition row 384 now includes a plurality of larger cells (i.e., hexagonal cells 384b and asymmetric cells 384a) through which blood may flow. These larger cells allow blood to flow unimpeded to the coronary arteries. Thus, the risk of paravalvular leakage is reduced while coronary perfusion is maximized.

Figure 4A:
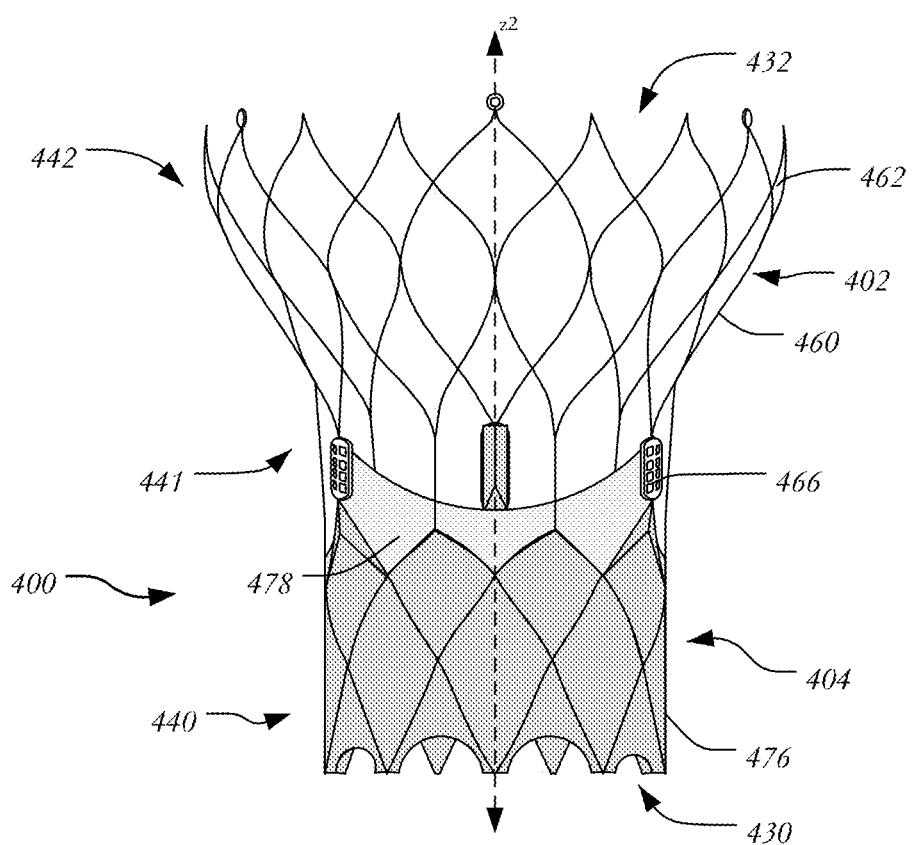
FIG. 4A is a side elevational view of a collapsible prosthetic heart valve having axial struts and auxiliary struts.

FIG. 4A illustrates another variation of a collapsible stent-supported prosthetic heart valve 400 capable of reducing paravalvular leakage and maximizing coronary perfusion. Heart valve 400 includes stent 402 and valve assembly 404 disposed within stent 402. Stent 402 generally extends between proximal end 430 and distal end 432 and includes annulus section 440 adjacent proximal end 430, aortic section 442 adjacent distal end 432, and transition section 441 between annulus section 440 and aortic section 442. Stent 402 may include a plurality of struts 460 forming cells 462, as well as commissure features 466. Valve assembly 404 may be disposed almost entirely within annulus section 440 as shown and includes a circumferential cuff 476 and a plurality of leaflets 478. Each leaflet 478 may be attached to cuff 476 and/or to selected struts 460 of stent 402, and to commissure features 466, while leaving a free edge for coapting with free edges of other leaflets 478 to form a one-way valve.

Figure 4B:
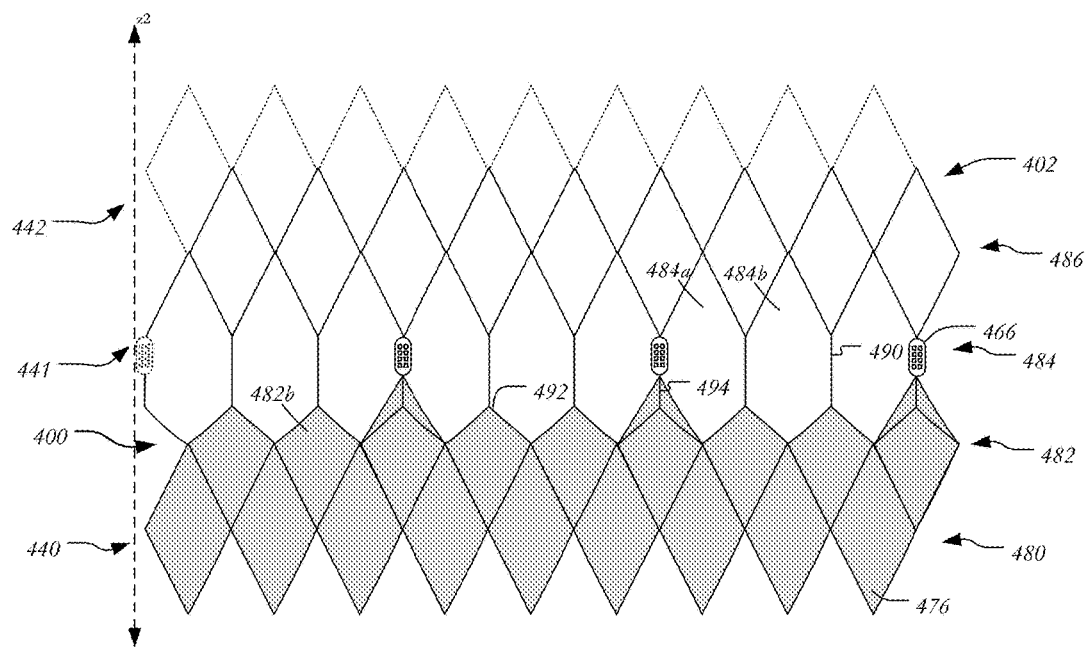
FIG. 4B is a schematic projection of a portion of the heart valve of FIG. 4A.

FIG. 4B is presented in order to appreciate the differences between heart valve 300 and heart valve 400. Heart valve 400 includes annulus section 440, transition section 441 and aortic section 442 of stent 402 (in dashed lines), commissure features 466 and cuff 476. For the sake of clarity, leaflets and remaining rows of aortic section 442 are not shown. Stent 402 includes a plurality of rows of cells including a first annular row 480, a second annular row 482, a transition row 484 and an aortic row 486. In contrast to heart valve 300 in which second annular row 382 has two types of cells (e.g., standard cells 382a and undersized cells 382b), second annular row 482 of heart valve 400 includes only undersized cells 482b. That is, all of the cells in second annular row 482 are the same size regardless of whether they are located below commissure features 466. Transition row 484 of heart valve 400 includes a plurality of hexagonal cells 484a, 484b. Hexagonal cells 484a are disposed adjacent commissure features 466 and are almost identical to hexagonal cells 484b, except that one side of each hexagonal cell 484a incorporates a commissure feature 466.

Specifically, heart valve 400 includes axial struts 490 in transition row 484, provided between commissure features 466. Axial struts may be oriented substantially parallel with central axis z2 of heart valve 400. Each axial strut 490 has a length that is greater than that of an adjacent commissure feature 466. Thus, in order to create a uniform second annular row 482 having uniform undersized cells 482b, auxiliary struts 494 are added directly below commissure features 466 and couple commissure features 466 to a cell in second annular row 482. Thus, each auxiliary strut 494 and adjacent comissure feature 466 may form one side of a cell.

In one example, the length of each axial strut 490 is equal to the sum of the lengths of one commissure feature 466 and one auxiliary strut 494. Because each axial strut 492 or commissure feature-auxiliary strut combination extends toward second annular row 482, shortened struts 492 form the upper struts of undersized cells 482*b*.

Cuff 476 may extend over all of the cells in first annular row 490 and second annular row 482. Thus, the addition of cuff 476 over undersized cells 482*b* aids in reducing paravalvular leakage due to less-than-perfect placement. Additionally, transition row 484 now includes a plurality of larger cells (e.g., hexagonal cells 484*a*, 484*b*) through which blood may flow unimpeded to the coronary arteries. As shown, cuff 476 extends over the length of auxiliary struts 494 to commissure features 466 and partially extends over hexagonal cell 484*a*. Thus, the risk of paravalvular leakage is reduced while coronary perfusion is maximized.

It will be appreciated that in one variation, the positions of commissure features 466 and auxiliary struts 494 may be switched. That is, commissure features 466 may be disposed proximal to auxiliary struts 494. In such examples, the geometry of cells such as those in first annular row 480, second annular row 482, transition row 484 and/or aortic row 486 may be adjusted to accommodate this change in position as well as the size and shape of cuff 476 and leaflets 478.

While the inventions herein have been described for use in connection with heart valve stents having a particular shape, the stent could have different shapes, such as a flared or conical annulus section, a less-bulbous aortic section, and the like, and a differently shaped transition section, Additionally, though the stent and cuff configurations have been described for use in connection with expandable transcatheter aortic valve replacement, they may also be used in connection with surgical valves, sutureless valves and other devices in which it is desirable to minimize paravalvular leakage, while maintaining proper blood flow at an outlet (e.g., at coronary arteries). It will also be understood that while the preceding disclosure has illustrated the use of a single cuff to cover two full rows of cells, multiple cuffs may be used. For example, a first cuff may be disposed about a first row of cells and a second cuff formed of the same or a different material than the first cuff may be disposed about a second row of cells. Additionally, a cuff may be disposed on either the luminal surface of the stent, the abluminal surface of the stent or both. A cuff may also include two layers (e.g., an inner layer on the luminal surface and an outer layer on the abluminal surface), the two layer being formed of different or the same material. The inner layer and the outer layer may also be formed of different thicknesses. For example, the inner layer may be formed thicker than the outer layer, or vice versa. Cuff thickness may also be varied from the proximal end of the heart valve to the distal end of the heart valve to decrease the crimp profile. When two layers are used, the two layers may be identical in geometry of different. Moreover, it will be understood that a cuff may extend beyond the proximal end of the stent. Without being bound to any particular theory, it is believed that combinations of these features may be used to enhance paravalvular sealing, reduce crimp profile and increase valve durability.

Moreover, although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

In some embodiments, a prosthetic heart valve, includes a collapsible and expandable stent including a plurality of struts forming cells, the stent having a proximal end, a distal end, an annulus section adjacent the proximal end, an aortic section adjacent the distal end, and a transition section disposed between the annulus section and the aortic section, the aortic section having a larger diameter than the annulus section. A valve assembly may be disposed entirely in the annulus section of the stent for controlling the flow of blood through the stent, the valve assembly including a plurality of leaflets, and a cuff, the cuff being disposed on a surface of the stent and extending fully over at least two rows of cells of the stout.

In some example, the cuff is disposed on a luminal surface of the stent; and/or the cuff is disposed about an abluminal surface of the stent; and/or the at least two rows of cells are disposed in the annulus section the stent; and/or the stent includes a plurality of commissure features and the at least two rows of cells include a first row and a second row, the second row having a plurality of primary cells and a plurality of undersized cells, each of the primary cells being disposed directly below one of the commissure features of the stent; and/or the stent includes three of the commissure features; and/or the at least two rows of cells include a first row adjacent the proximal end of the stent and a second row, the second row having a plurality of undersized cells that are smaller than cells of the first row; and/or cells in the transition section of the stent remain uncovered by the cuff to allow blood flow therethrough; and/or cells in the transition section are larger than cells in the annulus section; and/or the transition section includes cells having an asymmetric shape having an odd number of struts.

In some embodiments, a prosthetic heart valve may include a collapsible and expandable stoat including a plurality of struts forming cells, the stent having a proximal end, a distal end, an annulus section adjacent the proximal end, an aortic section adjacent the distal end, a transition section disposed between the annulus section and the aortic section, a plurality of commissure features and a plurality of axial struts oriented parallel to a longitudinal axis of the stent. A valve assembly may be disposed entirely in the annulus section of the stout for controlling the flow of blood through the stent, the valve assembly including a plurality of leaflets and a cuff, the cuff being disposed on a surface of the stent and extending fully over at least two rows of cells of the stent.

In some examples, the plurality of axial struts are disposed in the transition section; and/or the transition section includes multiple groups of cells, each group being disposed between adjacent commissure features and including a hexagonal cell and two asymmetric cells having an odd number of struts; and/or the annulus section includes undersized cells having a first group of struts with a first length and a second group of struts with a length less than the first length and the plurality of axial struts are coupled to struts in the second group; and/or each of the axial struts has a length that is greater than a length of one of the plurality of commissure features; and/or the transition section includes multiple groups of cells, each group being disposed between adjacent commissure features and including three hexagonal cells; and/or the heart valve further includes an auxiliary strut disposed below each of the plurality of commissure features; and/or the annulus section includes undersized cells having a first group of struts with a first length and a second group of struts with a length less than the first length, the struts in the second group being coupled to at least one of the plurality of axial struts or to one of the auxiliary struts;

and/or the annulus section includes at least one full row of the undersized cells, and the cuff extends fully over the full row of undersized cells; and/or each of the axial struts has a length that is equal to the sum of a length of one of the plurality of commissure features and a length of one of the auxiliary struts.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising: a collapsible and expandable stent including a plurality of struts forming cells arranged in annular rows and a plurality of commissure features circumferentially spaced about the stent in a predetermined one of the annular rows, the stent having a proximal end, a distal end, an annulus section adjacent the proximal end, an aortic section adjacent the distal end and having a larger diameter than the annulus section, and a transition section disposed between the annulus section and the aortic section, the transition section including a plurality of axial struts oriented parallel to a longitudinal axis of the stent and circumferentially spaced between the plurality of commissure features when the stent is in an expanded condition, the plurality of axial struts being disposed in the predetermined one of the annular rows and extending into the annulus section such that a proximal end of each of the axial struts is located closer to a proximal end of the stent than a proximal end of each of the commissure features is located to the proximal end of the stent, the stent having at least two annular rows of cells provided proximally of the proximal ends of the axial struts, a first one of the at least two rows including cells of a first size and a second one of the at least two rows including cells of a second size smaller than the first size, the plurality of axial struts being connected to the cells of the second size; and a valve assembly disposed entirely in the annulus section of the stent for controlling the flow of blood through the stent, the valve assembly including a plurality of leaflets, and a cuff, the cuff being disposed on a surface of the stent and extending fully over the at least two rows of cells.

2. The prosthetic heart valve of claim 1, wherein the cuff is disposed on a luminal surface of the stent.

3. The prosthetic heart valve of claim 1, wherein the cuff is disposed on an abluminal surface of the stent.

4. The prosthetic heart valve of claim 1, wherein the second one of the at least two rows of cells includes a plurality of primary cells, the primary cells being larger than the cells of the second size, each of the primary cells being disposed directly below one of the commissure features of the stent.

5. The prosthetic heart valve of claim 1, wherein the stent includes three of the commissure features.

6. The prosthetic heart valve of claim 1, wherein the first one of the at least two rows of cells is adjacent the proximal end of the stent.

7. The prosthetic heart valve of claim 1, wherein cells in the transition section of the stent remain uncovered by the cuff to allow blood flow therethrough.

8. The prosthetic heart valve of claim 1, wherein cells in the transition section are larger than cells in the annulus section.

9. The prosthetic heart valve of claim 1, wherein the transition section includes cells having an asymmetric shape.

10. The prosthetic heart valve of claim 1, wherein the transition section includes multiple groups of cells, each group being disposed between adjacent commissure features and including a hexagonal cell and two asymmetric cells having an odd number of struts.

11. The prosthetic heart valve of claim 1, wherein the cells of the second size include a first group of struts with a first length and a second group of struts with a length less than the first length and the plurality of axial struts are coupled to struts in the second group.

12. The prosthetic heart valve of claim 1, wherein each of the axial struts has a length that is greater than a length of one of the plurality of commissure features.

13. The prosthetic heart valve of claim 1, wherein the transition section includes multiple groups of cells, each group being disposed between adjacent commissure features and including three hexagonal cells.

14. The prosthetic heart valve of claim 1, further comprising an auxiliary strut disposed below each of the plurality of commissure features.

15. The prosthetic heart valve of claim 14, wherein the cells of the second size include a first group of struts with a first length and a second group of struts with a length less than the first length, the struts in the second group being coupled to at least one of the plurality of axial struts or to one of the auxiliary struts.

16. The prosthetic heart valve of claim 14, wherein each of the axial struts has a length that is equal to the sum of a length of one of the plurality of commissure features and a length of one of the auxiliary struts.

* * * * *